United States Patent
Oyama

(10) Patent No.: US 7,084,772 B2
(45) Date of Patent: Aug. 1, 2006

(54) WAKEFULNESS ESTIMATING APPARATUS AND METHOD

(75) Inventor: Hajime Oyama, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 156 days.

(21) Appl. No.: 10/925,273

(22) Filed: Aug. 24, 2004

(65) Prior Publication Data

US 2005/0046579 A1    Mar. 3, 2005

(30) Foreign Application Priority Data

Aug. 26, 2003    (JP) .............................. 2003-301998

(51) Int. Cl.
*G08B 13/18* (2006.01)

(52) U.S. Cl. ...................... 340/575; 340/575; 600/554; 600/555; 600/558

(58) Field of Classification Search ................ 340/575, 340/576, 554, 439; 600/554, 555, 558; 348/148
See application file for complete search history.

(56) References Cited

U.S. PATENT DOCUMENTS

| | | | |
|---|---|---|---|
| 5,642,093 A * | 6/1997 | Kinoshita et al. | 340/439 |
| 5,890,083 A | 3/1999 | Franke et al. | |
| 5,923,256 A * | 7/1999 | Satake et al. | 340/575 |
| 6,281,808 B1 | 8/2001 | Glier et al. | |
| 6,317,057 B1 | 11/2001 | Lee | |
| 6,335,689 B1 * | 1/2002 | Mine | 340/576 |
| 6,686,845 B1 * | 2/2004 | Oyama | 340/575 |
| 2004/0080422 A1* | 4/2004 | Oyama | 340/576 |
| 2004/0262063 A1* | 12/2004 | Kaufmann et al. | 180/169 |

FOREIGN PATENT DOCUMENTS

| | | |
|---|---|---|
| EP | 1 209 019 A2 | 5/2002 |
| JP | 2002-154345 A1 | 5/2002 |
| JP | 2002-163642 A1 | 6/2002 |

* cited by examiner

*Primary Examiner*—Jeffery Hofsass
*Assistant Examiner*—Hoi C. Lau
(74) *Attorney, Agent, or Firm*—Darby & Darby

(57) ABSTRACT

An estimated value of wakefulness is calculated from the ratio between the quantity of high frequency components and the quantity of low frequency components obtained by performing frequency transformation of vehicle displacements (S51). An imaginary deviation line is set between a lane marking and the vehicle according to the estimated value of wakefulness (S55, S59, S62, S66), and an alarm is issued when the vehicle deviates from the imaginary deviation line. Since the alarm is issued when the vehicle is at a predetermined distance from the lane marking, alarming can be performed at substantially constant timing.

12 Claims, 11 Drawing Sheets

WAKEFULNESS ESTIMATING APPARATUS AND METHOD

BACKGROUND OF THE INVENTION

The present invention relates to an apparatus and a method for estimating the level of wakefulness of a driver from displacements of the vehicle body in a lateral direction thereof.

The development of techniques for preventing accidents attributable to a reduction in the wakefulness of drivers is one of important subjects from the viewpoint of safety, and various methods for detecting a reduction of wakefulness and alarming techniques associated therewith have been conceived and put in use.

In JP-A-2002-154345, the applicant has proposed a technique associated with estimation of wakefulness for allowing the level of wakefulness of a driver to be accurately determined in the presence of significant changes in the driving environment and vehicle speed.

According to the wakefulness estimating technique disclosed in JP-A-2002-154345, displacements of a vehicle in the width direction of the vehicle are detected at first as a time series; the displacements are subjected to frequency transformation to calculate the quantities of frequency power components; and an average value of the quantities of frequency power components is calculated as the quantity of high frequency components. At the same time, a maximum value of the quantities of frequency power components within a predetermined frequency range including a stagger frequency exposed when the driver is at a low level of wakefulness is calculated as the quantity of low frequency components.

Then, the level of wakefulness of the driver is determined based on the ratio of the quantity of high frequency components to the quantity of low frequency components.

According to JP-2002-154345, the wakefulness of a driver is determined to be low when the quantity of high frequency components is small and the quantity of the low frequency components is great.

However, wakefulness is not instantaneously determined, but a reduction in the level of wakefulness or the like is estimated by comparing a phenomenon of a certain level that has appeared with a threshold.

In general, a wakefulness estimating apparatus of this type issues an alarm as soon as a reduction in the level of wakefulness is determined to warn the driver. However, the timing of such an alarm is not stable, which lets a driver feel uncomfortable.

An active driver assist system (ADA) recognizes left and right lane markings located ahead the vehicle in the traveling direction thereof based on an image obtained by a camera loaded on the vehicle and issues an alarm to warn the driver when the vehicle deviates from the lane markings.

However, it is difficult for a driver at a low level of wakefulness to properly perform an avoiding operation when an alarm is issued at the time of a deviation from a lane marker (a white line).

SUMMARY OF THE INVENTION

The invention confronts situations as described above, and it is an object of the invention to provide an apparatus and a method for estimating wakefulness of a driver which allow an alarm according to the level of wakefulness of a driver to be issued at substantially constant timing so that the driver will not feel uncomfortable.

In order to achieve the above-described object, an apparatus for estimating wakefulness of a driver according to the invention includes: a frequency analyzing process unit which performs frequency transformation of displacements of a vehicle in the width direction of the vehicle detected as a time series to calculate the quantities of frequency power components, calculates an average value of the quantities of the frequency power components as a quantity of high frequency components, and calculates a maximum value of the quantities of frequency power components within a predetermined frequency range including a stagger frequency exposed when the driver is at a low level of wakefulness, the maximum value being calculated as a quantity of low frequency components; an estimated wakefulness value calculation unit which calculates an estimated value of wakefulness from the ratio of the quantity of high frequency components to the quantity of low frequency components; and an alarm control unit which sets an imaginary deviation line between a lane marking extending on a side the vehicle and the vehicle with a predetermined interval from the lane marking according to the estimated value of wakefulness and issues an alarm when a deviation from the imaginary deviation line occurs.

According to the invention, an alarm according to the level of wakefulness of a driver can be issued at substantially constant timing, which is very much advantageous, for example, in that the driver will not feel uncomfortable.

DESCRIPTION OF THE PREFERRED EMBODIMENT

An embodiment of the invention will now be described based on the drawings.

Prior to a specific description of a wakefulness estimating apparatus, a fundamental principle underlying a method of estimating wakefulness in the present embodiment will be described with reference to FIGS. 1A, 1B, 2A and 2B.

Figure 1A:
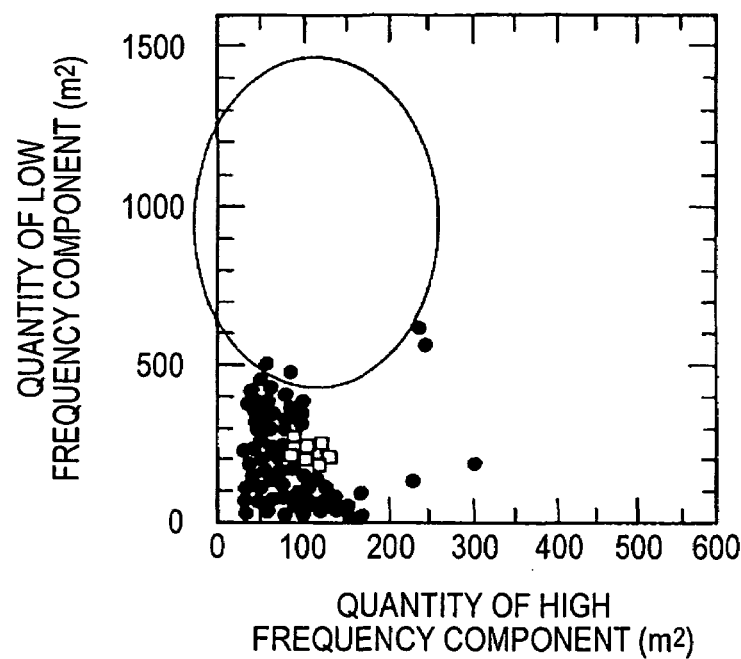
FIGS. 1A and 1B show distribution characteristics of frequency components obtained from a driver who drives with less staggering when the driver is sleepy.
Figure 1B:
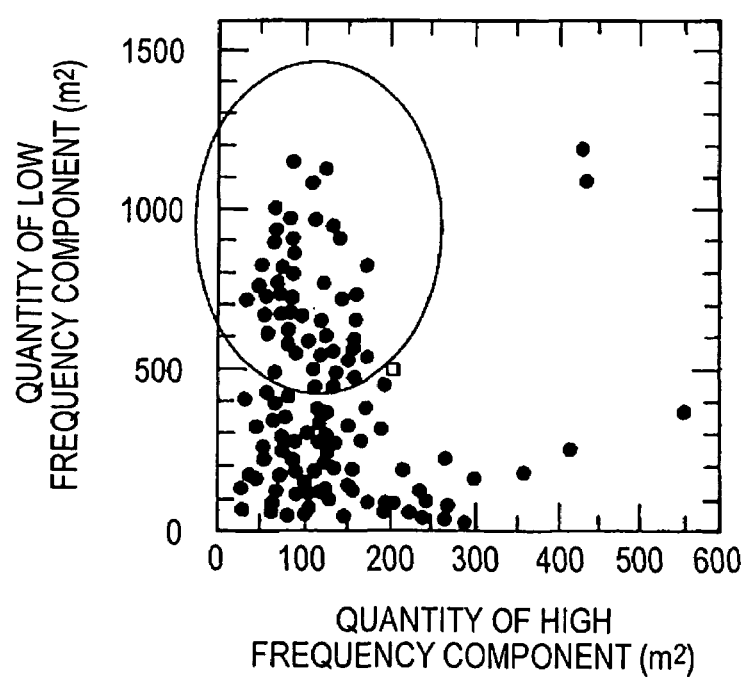
Figure 2A:
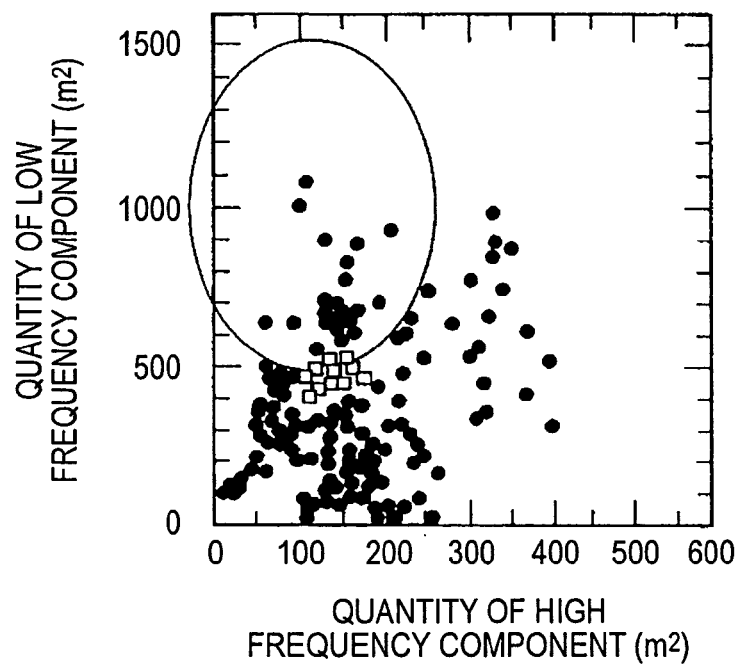
FIGS. 2A and 2B show distribution characteristics of frequency components obtained from a driver who drives with more staggering when the driver is not sleepy.
Figure 2B:
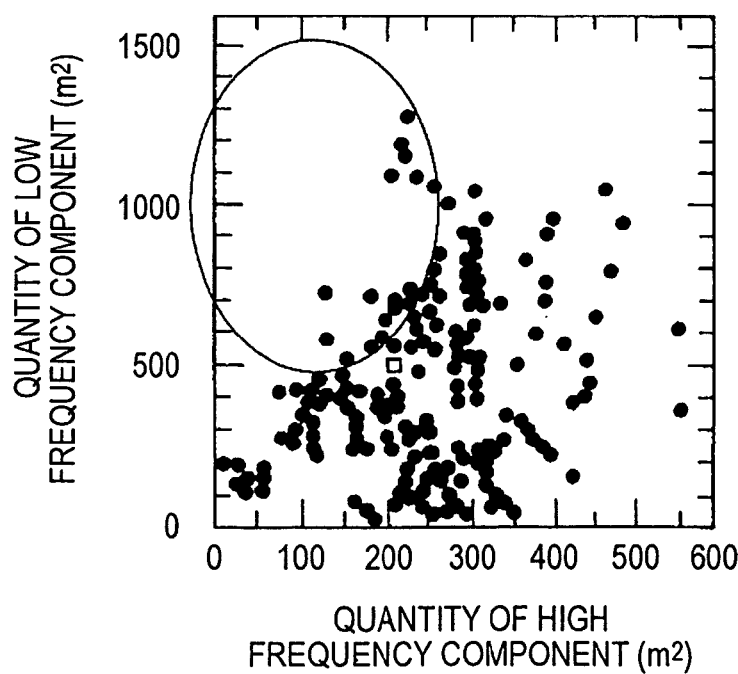

FIGS. 1A and 1B show examples of graphs showing distribution characteristics of the quantities of frequency components obtained from a driver who drives with less staggering and who is sleepy, and FIGS. 2A and 2B show examples of graphs showing distribution characteristics of the quantities of frequency components obtained from a driver who drives with more staggering and who is not sleepy. The abscissa axes represent the quantities of high frequency components, and the ordinate axes represent the quantities of low frequency components.

In the figures, a black dot is plotted to indicate a coordinate point (a frequency component quantity point) represented by the quantity of high frequency components calculated at a certain time and the quantity of low frequency components calculated at the same time.

The term "the quantities of frequency components" means the quantities of discrete frequency power components which are obtained by performing frequency transformation of displacements of a vehicle in the width direction of the vehicle detected as a time series. In a normal state of driving, since steering is intentionally performed because of curves of the road, the quantities of components on the side of relatively high frequencies (the quantities of high frequency components) tend to steadily appear over a frequency range. In the present embodiment, a calculated average value of the quantities of the frequency power components is referred to as "the quantity of high frequency components".

On the contrary, the quantities of components on the side of relatively low frequencies (the quantities of low frequency components) tend to appear in a state of driving at a low level of wakefulness. In the present embodiment, a maximum value of the quantities of frequency power components within a predetermined frequency range is referred to as "the quantity of low frequency components". The frequency range is a low frequency band including a stagger frequency, the band being set based on the stagger frequency as will be described later.

The region enclosed by an ellipse is a region which has a significant influence on the estimation of wakefulness or a region having a small quantity of high frequency components and a large quantity of low frequency components. As the wakefulness of a driver becomes lower, the number of frequency component quantity points present in the elliptic region increases. A value (expressed by P'slp/P'ave as described later) obtained by dividing the quantity of the low frequency components by the quantity of high frequency components becomes larger, the lower the wakefulness of the driver becomes.

Let us now consider the state of wakefulness of a driver who drives with less staggering when the driver is sleepy as shown in FIGS. 1A and 1B. FIG. 1A shows distribution characteristics represented by plotting calculated frequency component quantity points (the quantities of high frequency components and the quantities of low frequency components) as they are. The characteristics of a driver of this type inherently include a smaller number of low frequency components in comparison to the characteristics of an average driver.

For this reason, the number of frequency component quantity points that appear in the region enclosed by the ellipse may not be so large even during a travel at a low level of wakefulness. As a result, it may be erroneously determined that there is no reduction in wakefulness in spite of the reduction of wakefulness.

Let us now consider the state of wakefulness of a driver who drives with more staggering when the driver is not sleepy as shown in FIGS. 2A and 2B. FIG. 2A shows distribution characteristics represented by plotting calculated frequency component quantity points (the quantities of high frequency components and the quantities of low frequency components) as they are. The characteristics of a driver of this type inherently include a large number of low frequency components in comparison to the characteristics of an average driver.

For this reason, a large number of frequency component quantity points may appear in the region enclosed by the ellipse even during a travel without any reduction of wakefulness. As a result, it may be erroneously determined that there is a reduction of wakefulness in spite of fact that there is no reduction of wakefulness.

The erroneous determinations in the above-described two cases are attributable to the fact that no consideration is paid to characteristics unique to each driver associated with stagger. Characteristics unique to a driver are reflected in low frequency percentile values and high frequency percentile values.

A white square point shown in any of FIGS. 1A to 2B indicates a coordinate point (percentile point) represented by plotting a high frequency percentile value calculated at a certain time and a low frequency percentile value calculated at the same time. A percentile point (a high frequency percentile value and a low frequency percentile point) calculated at a certain time is in a significant correlation with a frequency component quantity point (the quantity of high frequency components and the quantity of low frequency components) calculated at the same time.

The term "high frequency percentile value" means a percentile value at which the sum of frequencies of occurrence of the quantities of frequency power components in a histogram of high frequency components counted from the lowest value reaches a predetermined ratio to the sum total of such frequencies. In one process of driving performed by one driver, the high frequency percentile value fluctuates by a relatively small amount and tends to be substantially constant (the value is substantially independent on the state of wakefulness of the driver).

In the present embodiment, the predetermined ratio is 80% i.e., an 80-percentile value is used. However, this value is merely an example, and the ratio is required only to stay in the range from 70 to 90% (this holds true for a low frequency percentile value to be described below).

The term "low frequency percentile value" means a percentile value (e.g., 80-percentile value) at which the sum of frequencies of occurrence of the quantities of frequency power components in a histogram of low frequency components integrated from the lowest value reaches a predetermined ratio to the sum total of such frequencies.

The low frequency percentile value fluctuates greatly unlike the characteristics of the high frequency percentile value, and the fluctuation tends to become significant as the level of wakefulness decreases. The ratio between the high frequency percentile value and the low frequency percentile value tends to be constant as long as the driver is wakeful.

As a result of a driving test conducted on a large number of drivers and a close study on resultant driving data, it was revealed that the percentile point (high frequency percentile value and low frequency percentile value) of an average driver (an imaginary driver who has the driving characteristics of the highest frequency of occurrence) was (200, 400 to 500).

The high frequency percentile value of an average driver is hereinafter referred to as "standard high frequency percentile value", and the value is assumed to be 200 in the present embodiment. The low frequency percentile value of an average driver is referred to as "standard low frequency percentile value, and the value is assumed to be 500 in the present embodiment.

The percentile point of an average driver is referred to as "standard percentile point". The ratio of the standard low frequency percentile value to the standard high frequency percentile value is only required to stay in the range from 2 to 2.5 times, and the standard percentile point may be set at (200, 400), for example.

It will be understood that percentile points (high frequency percentile values and low frequency percentile values) in the case shown in FIG. 1A were concentrated in the neighborhood of the values (100, 250). In the light of the fact that the percentile point of an average driver was (200, 500), a driver having characteristics as shown in FIG. 1A may be determined to be a driver who inherently drives with less staggering.

It will be understood that percentile points (high frequency percentile values and low frequency percentile values) in the case shown in FIG. 2A were concentrated in the ranges of values (100 to 200, 400 to 600). In the light of the fact that the percentile point of an average driver was (200, 500), a driver having characteristics as shown in FIG. 2A may be determined to be a driver who inherently drives with more staggering.

In the present embodiment, each frequency component quantity point is shifted by vertical and horizontal ratios between a calculated percentile point and a standard percentile point to normalize the frequency component quantity point.

For example, let us consider a frequency component quantity point (100, 500) in FIG. 1A. In this case, when a percentile point (100, 250) is associated with the frequency component quantity point, the vertical and horizontal ratios of the standard percentile point (200, 500) to that percentile point are 2.0 times in the horizontal and vertical directions. As a result, the frequency component quantity point will be on a coordinate of (100×2.0, 500×2.0) or (200, 1000) after it is shifted.

When such shifting is carried out for all frequency component quantity points, the distribution characteristics shown in FIG. 1A are corrected into the distribution characteristics shown in FIG. 1B. Since a large number of frequency component quantity points appear in the region enclosed by the ellipse as a result of such a correction, it is possible to effectively prevent an erroneous determination on a driver who inherently drives with less staggering.

The distribution characteristics shown in FIG. 2A are similarly shifted. For example, let us consider a frequency component quantity point (100, 1000) in FIG. 2A. In this case, when a percentile point (100, 500) is associated with the frequency component quantity point, the vertical and horizontal ratios of the standard percentile point (200, 500) to that percentile point are 2.0 times in the horizontal direction and 1.0 times in the vertical direction.

As a result, the frequency component quantity point will be on a coordinate of (100×2.0, 1000×1.0) or (200, 1000) after it is shifted. When such shifting is carried out for all frequency component quantity points, the distribution characteristics shown in FIG. 2A are corrected into the distribution characteristics shown in FIG. 2B. Since the number of frequency component quantity points that appear in the region enclosed by the ellipse is reduced as a result of such a correction, it is possible to effectively prevent an erroneous determination on a driver who inherently drives with more staggering.

The quantities of high frequency components and the quantities of low frequency components are corrected using the vertical and horizontal ratios between calculated percentile points and a standard percentile point as described above. All drivers can be thus treated equally to an average driver regardless of differences between the drivers in staggering at driving. As a result, the level of wakefulness of a driver can be more accurately determined.

When a driver traveling on an expressway encounters a section with consecutive curves such as those in mountains, since the steering wheel is turned to the left and right many times, the quantity of stagger increases. FIGS. 3A to 3E show data collected when a wakeful driver traveling on an expressway transfers from a travel on a straight road to a travel on curves whose winding direction continuously changes.

Figure 3A:
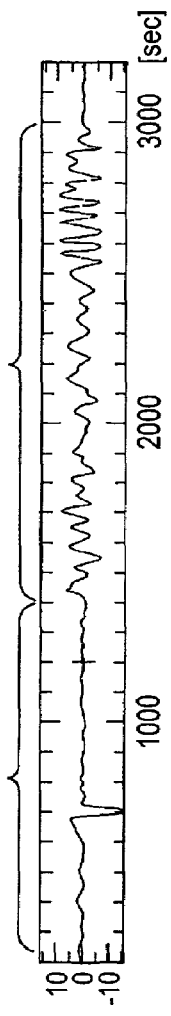
FIGS. 3A to 3E are graphs showing characteristics observed during a straight-ahead travel and a travel on successive curves on an expressway.
Figure 3B:
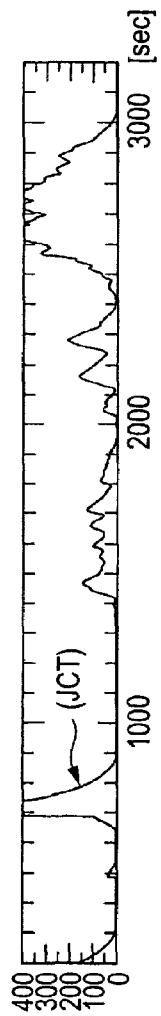

FIG. 3A indicates quantities of steering during the travel with a positive sign assigned for leftward steering and a negative sign assigned for the rightward steering. FIG. 3B shows additional steering values. The part with a great change of the additional steering value in the straight traveling section in FIG. 3B represents a travel through a junction.

Figure 3C:
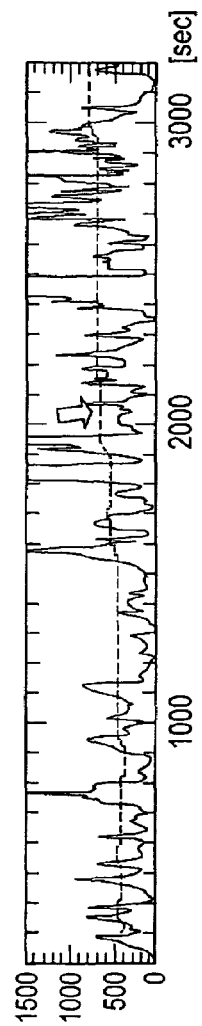

As shown in FIG. 3C, frequency band power values associated with wakefulness are obtained based on additional steering values, and 80-percentile values of the quantities of frequency power components are plotted. The 80-percentile values are high as indicated by an arrow during the travel on curves with a successively changing winding direction. Therefore, estimation of wakefulness of the driver may result in an erroneous determination indicating a reduction in wakefulness. The high 80-percentile values are considered attributable to the fact that curvatures of an expressway running in mountains have some pattern and that turns of the driving wheel appear in a certain pattern.

Figure 3D:
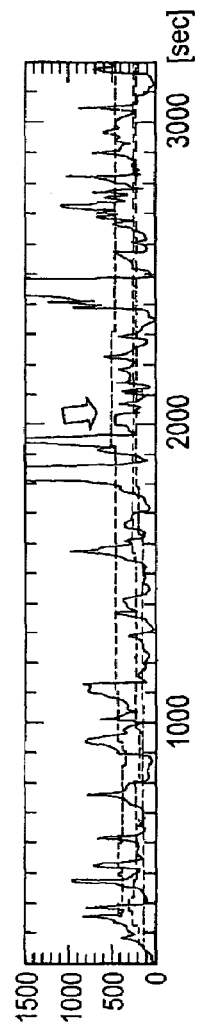

In the present embodiment, therefore, wakefulness H to be described later that indicates the level of wakefulness of a driver is corrected during a travel on curves of an expressway, so that 80-percentile value substantially equal to those in a travel on a straight road will appear as shown in FIG. 3D.

Figure 4:
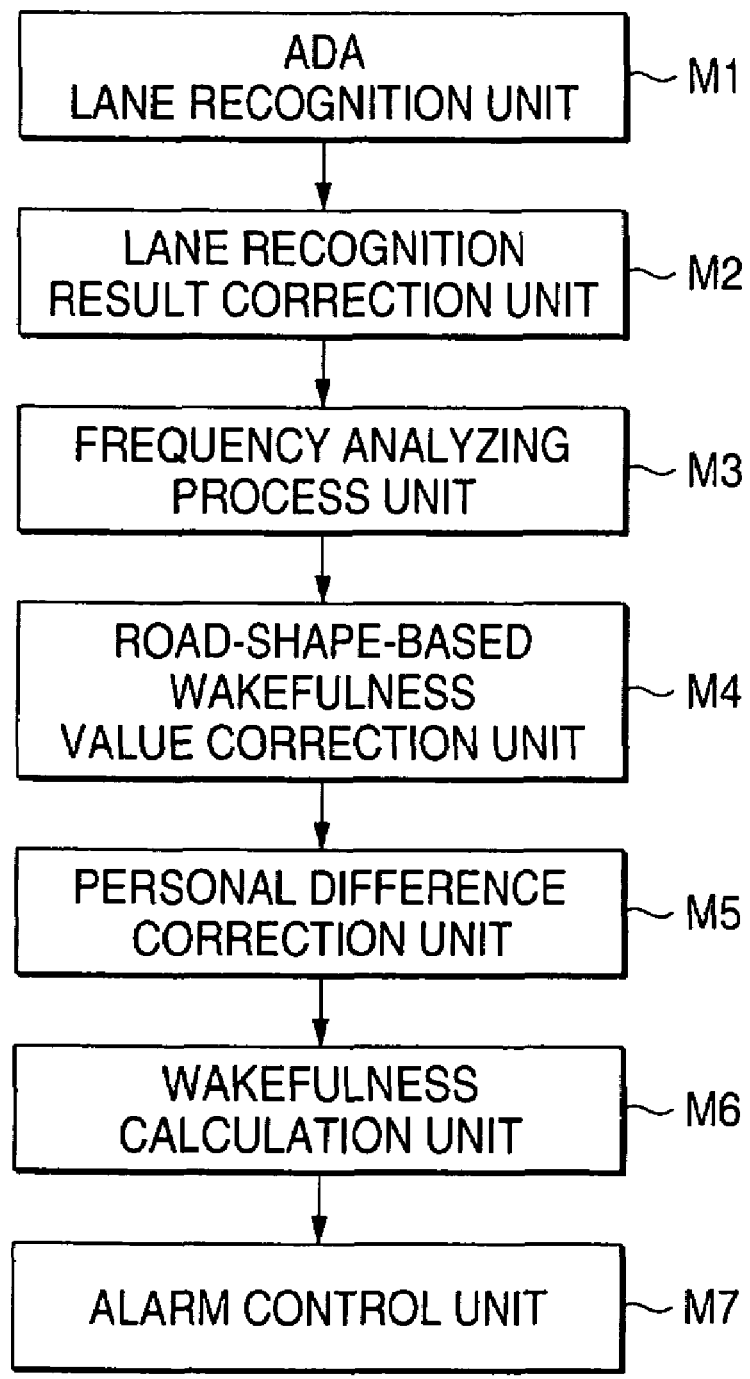
FIG. 4 is a functional block diagram of a wakefulness estimating apparatus.

A wakefulness estimating apparatus loaded on a vehicle will now be described with reference to FIG. 4. The wakefulness estimating apparatus has an ADA lane recognition unit M1, a lane recognition result correction unit M2, a frequency analyzing process unit M3, a road-shape-based wakefulness correction unit M4, a personal difference correction unit M5, a wakefulness calculation unit M6, and an alarm control unit M7.

The ADA lane recognition unit M1 utilizes an automatic drive assist (ADA) system to recognize left and right lane markings located ahead the vehicle in the traveling direction thereof based on an image obtained by a stereoscopic camera or single-lens camera utilizing a CCD (solid-state image pickup device) loaded on the vehicle.

In order to obtain accurate data on displacements in the lane, the lane recognition result correction unit M2 identifies the type of the lane markings drawn on the road as any of a plurality of preset lane marking types based on a recognized lane width obtained from the difference between the positions of the left and right lane markings recognized by the ADA lane recognition unit M1 and detects displacements (lateral displacements) of the vehicle in the direction of the vehicle width based on the lane marking type thus identified.

Steps for calculating displacements of a vehicle are described in detail in JP-A-2002-163642 previously submitted by the applicant.

Figure 5:
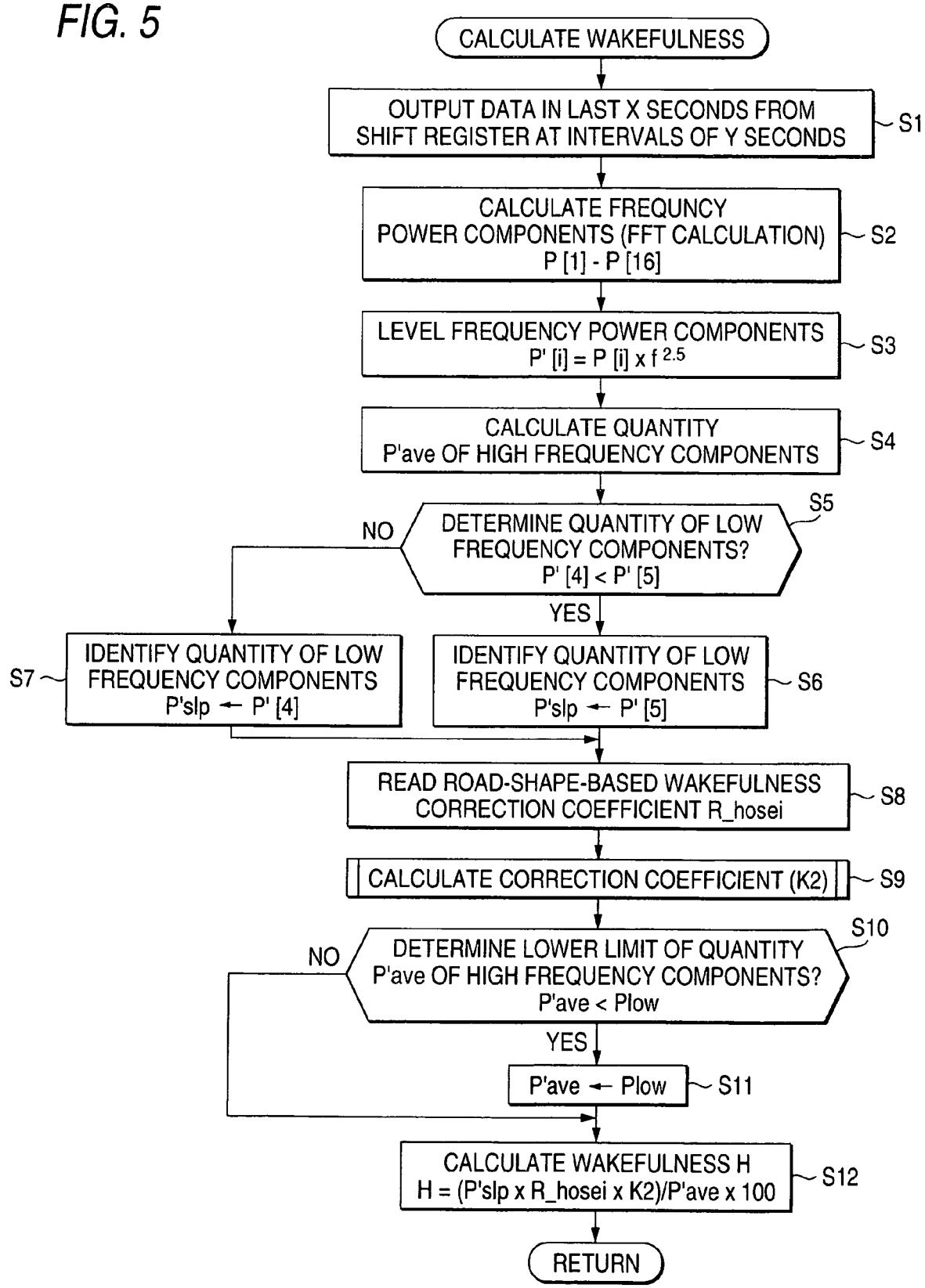
FIG. 5 is a flow chart showing a wakefulness calculation routine.

Functions of the frequency analyzing process unit M3, the road-shape-based wakefulness correction unit M4, the personal difference correction unit M5, the wakefulness calculation unit M6, and the alarm control unit M7 are realized by an electronic control unit (ECU). The functions of the units M3 to M7 will now be described with reference to and in association with a wakefulness calculation routine that is shown in FIG. 5. The routine is repeatedly executed on a predetermined cycle.

The frequency analyzing process unit M3 performs processes at steps S1 to S6. First, it reads data of displacements in the last X seconds stored in a shift register at intervals of Y seconds (e.g., 90 seconds or shorter) at step S1. For accurate estimation of wakefulness, a somewhat long time (e.g., about 50 to 80 seconds) is preferably set as the sampling time X.

At step S2, the displacements (lateral displacements) which have been detected as a time series are subjected to frequency transformation using fast Fourier transform (FFT) to calculate the quantities (amplitudes) P[i] of frequency power components in the frequency spectrum. In the present embodiment, the quantities P[1] to P[16] of sixteen frequency power components are calculated at intervals of 0.02 Hz in a frequency range from 0.03 to 0.3 Hz. The reason for neglecting the frequency range lower than the 0.03 Hz is the fact that power in that range tends to increase during a travel on curves and has no direct relationship with the level of wakefulness of the driver. The frequency range higher than 0.3 Hz is neglected to reduce the amount of calculations required to calculate wakefulness H because power in that frequency range is normally negligibly small.

At step S3, the quantities P[i] of the frequency power components in the frequency range from 0.03 to 0.3 Hz (i=1 to 16) are leveled according to the following equation to calculate leveled quantities P'[i] of the frequency power components.

$$P'[i] = P[i] \cdot f^n \qquad \text{Equation 1}$$

where the exponent n satisfies $2.0 \leq n \leq 3.0$.

When it is assumed that a staggering of a vehicle in a lane is one of many kinds of fluctuations that exist in the natural world, it has an amplitude of 1/f and power of $1/f^2$. Therefore, the exponent n in Equation 1 may theoretically be 2.0, but it is preferably set at 2.5 from results of experiments. This is considered attributable to vehicle specifications, differences in driving between individual drivers, and influences of road conditions. However, the wakefulness of a driver can be determined using any exponent within the range from 2.0 to 3.0. The exponent n is set at 2.5 in the present embodiment.

Figure 9A:
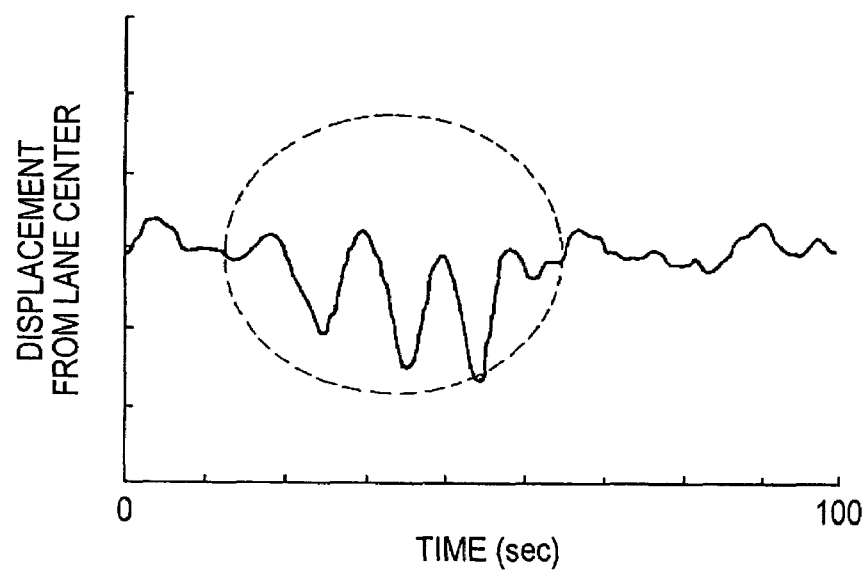
FIGS. 9A and 9B are graphs for explaining calculation of wakefulness.
Figure 9B:
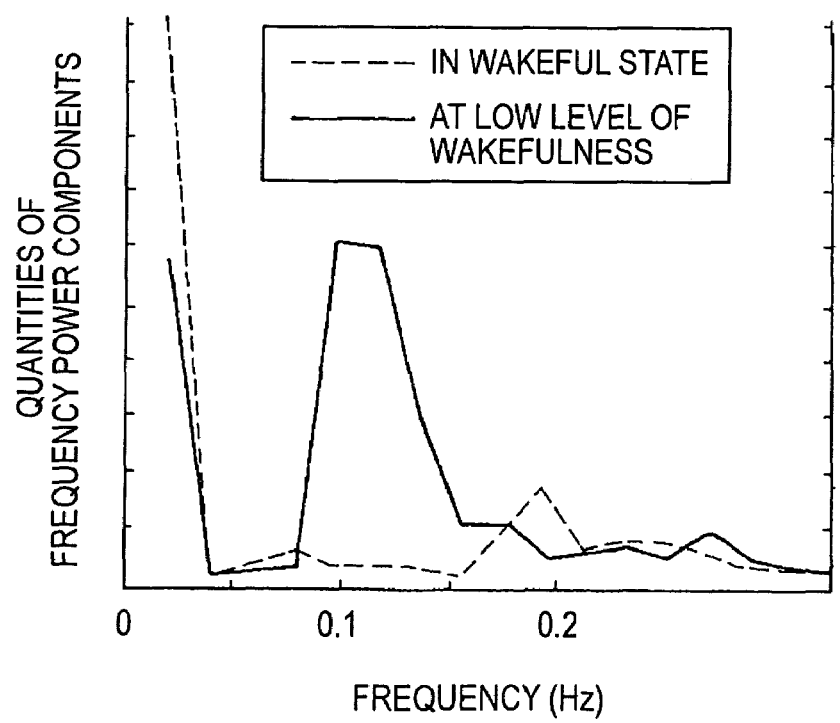

General characteristics can be visually observed on the distribution of the leveled quantities P'[i] of the frequency power components. Specifically, when a staggering that is characteristic of a reduction of wakefulness is detected about 50 minutes after the beginning of detection as shown in FIG. 9A, it will be understood from the relationship between frequency components i[Hz] and leveled quantities P'[i] of the frequency power components as shown in FIG. 9B that there is an abrupt increase in the quantities P'[i] of the frequency power components in the neighborhood of 0.1 Hz that is a low frequency range as a stagger frequency f1.

When the wakefulness of a driver is low, there is a tendency that power in the neighborhood of the stagger frequency f1 exposed in lateral displacements of the vehicle. In other words, the state of low wakefulness is characterized in that only power in the low frequency range including the stagger frequency f1 increases while levels in other ranges are low. The wakefulness of the driver can be determined by comparing the peak of the power in the neighborhood of the stagger frequency f1 and the state of power in other frequency ranges taking such a tendency into consideration.

The term "stagger frequency f1" means a frequency exposed (or converging) when a driver is in states of low wakefulness (including the state of driving asleep). In general, the frequency tends to appear with a value in the range from 0.08 to 0.12 Hz in the case of a passenger car. In practice, however, the frequency is set at an appropriate value for each type of cars through experiments and simulations because it is influenced by characteristics and speeds of vehicles. In the present embodiment, the stagger frequency f1 is set at 0.1 Hz.

At step S4, the sum total of the quantities P'[1] to P'[16] of the frequency power components is obtained to calculate an average value thereof as a quantity P'ave of high frequency components. In the present embodiment, in order to allow the level of wakefulness of the driver to be more accurately reflected in wakefulness H to be described later, the quantity having the maximum power is excluded from the quantities P'[1] to P'[16] of the frequency power components, and the quantity P'ave of high frequency power components is calculated from the remaining quantities P'[i] of the frequency power components. The purpose of such filtering is to eliminate the influence of an increase in the power of the stagger frequency f1 and the influence of disturbances.

At step S5, the power of the stagger frequency is determined. That is, the magnitudes of the quantities P'[4] and P'[5] of frequency power components in a predetermined frequency range (0.09 to 0.11 Hz) that includes the stagger frequency f1 (0.1 Hz) are compared. The smaller power component quantity is set as a quantity P'slp of low frequency power components.

Specifically, when the power component quantity P'[5] at 0.11 Hz is smaller than the power component quantity P'[4] at 0.09 Hz, the process proceeds to step S6 to set the power component quantity P'[5] as the quantity P'slp of low frequency components.

When the power component quantity P'[5] at 0.11 Hz is equal to or greater than the power component quantity P'[4] at 0.09 Hz, the process proceeds to step S7 to set the power component quantity P'[4] as the quantity P'slp of low frequency components.

The combination of the quantity P'ave of high frequency components and the quantity P'slp of low frequency components calculated at steps S4 to S7 is stored in a shift register.

The process then proceeds to step S8. At step S8, a road-shape-based wakefulness correction coefficient calculation routine is executed, the routine being processed by the road-shape-based wakefulness correction unit M4. This routine is executed according to the flow chart shown in FIG. 6.

First, a subtraction is carried out on an integrated value dakaku_sum based on the following equation at step S21. The integrated value dakaku_sum is given by step S23 or step S24 to be described later, and it is set according to steering angles dakaku detected by a steering angle sensor as steering angle detection means.

$$dakaku\_sum \leftarrow dakaku\_sum - ((dakaku\_sum/500)+1) \qquad \text{Equation 2}$$

The process then proceeds to step S22 to read a steering angle dakaku detected by the steering angle sensor and to compare the absolute value of the same with a determination steering angle of 15°. The determination steering angle of 15° is a value for checking whether the vehicle is traveling a curve having a relatively small radius of curvature such as a junction of an expressway. The value is not limiting the invention, and a value greater or smaller than the same may be used.

When |dakaku|>15, the process proceeds to step S23 at which a preset great steering angle value of 45 is added to the integrated value dakaku_sum on which a subtraction has been carried out at step S21 (dakaku_sum←dakaku_sum+ 45).

When |dakaku|≦15, the process branches to step S24 at which ((dakaku)$^2$/5) is added to the integrated value dakaku_sum calculated at step S21 (dakaku_sum→dakaku_sum+(dakaku)$^2$/5)

Since the process of squaring the steering angle dakaku is performed only to calculate the absolute value of the same, the absolute value of the steering angle dakaku may alternatively be added directly.

During a travel on a road on which steering is performed many times or a travel on curves whose winding direction successively changes, the steering wheel is turned at the entrance of the next curve when |dakaku|>0. Thus, the absolute value |dakaku| gradually approaches 0, equals 0 soon, and becomes greater than 0 when the next curve is traveled. This is repeated when curves appear successively.

During a travel on a curve having a relatively small radius of curvature such as a junction, since the steering angle dakaku is greatly inclined in one direction, the preset great steering angle value 45 is integrated each time the routine is repeated.

The process then proceeds to step S25, and the shape of the road is determined based on the integrated value dakaku_sum at steps S25 and S26.

Specifically, the integrated value dakaku_sum is compared with a great determination value of 1500 at step S25, and the integrated value dakaku_sum is compared with a small determination value of 150 at step S26.

When dakaku_sum>1500, the process proceeds to step S27 at which the process exits the routine after a stagger alarm is halted.

The great steering angle determination value 1500 is a value for determining whether the road shape represents a road having a relatively small radius of curvature such as an interchange or junction or an ordinary road. When dakaku≧1500, a stagger alarm which will be described later is halted because the estimation of wakefulness is disabled by consecutive great steering angles.

When 150<dakaku_sum<1500, the process proceeds to step S28 at which the process exits the routine after a road-shaped-based wakefulness correction coefficient R_hosei is set at 0.5 (R_hosei←0.5).

When 150<dakaku_sum<1500, it is assumed that steering is successively performed at small steering angles and that the shape of the expressway is consecutive curves in different directions. Therefore, the road-shape-based wakefulness correction coefficient R_hosei is set at 0.5. The road-shape-based wakefulness correction coefficient R_hosei is read in when wakefulness H to be described later is calculated.

When dakaku_sum≦150, the process proceeds to step S29 at which the process exits the routine after the road-shape-based correction coefficient R_hosei is set at 1 (R_hosei←1).

When dakaku_sum≦150, since it is assumed that the vehicle is traveling straight on the expressway, normal calculations are carried out with the road-shape-based wakefulness correction coefficient set at 1.

Figure 3E:
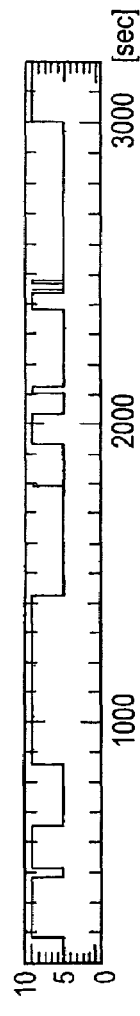

FIG. 3E shows changes in the road-shape-based wakefulness correction coefficient R_hosei that occur during an actual travel on an expressway. During a travel on curves whose winding direction successively changes, the road-shape-based wakefulness correction coefficient R_hosei is set at 0.5 in a region having a high 80-percentile value as indicated by the arrow in FIG. 3C. As a result, the 80-percentile value is corrected using the road-shape-based wakefulness correction coefficient R_hosei to a value equivalent to that for a straight travel as shown in FIG. 3D.

When the process proceeds to step S9 shown in FIG. 5, a process at the personal difference correction unit M5 is performed. Specifically, a correction coefficient K2 is calculated based on the quantity P'ave of high frequency components and the quantity P'slp of low frequency components.

Figure 7:
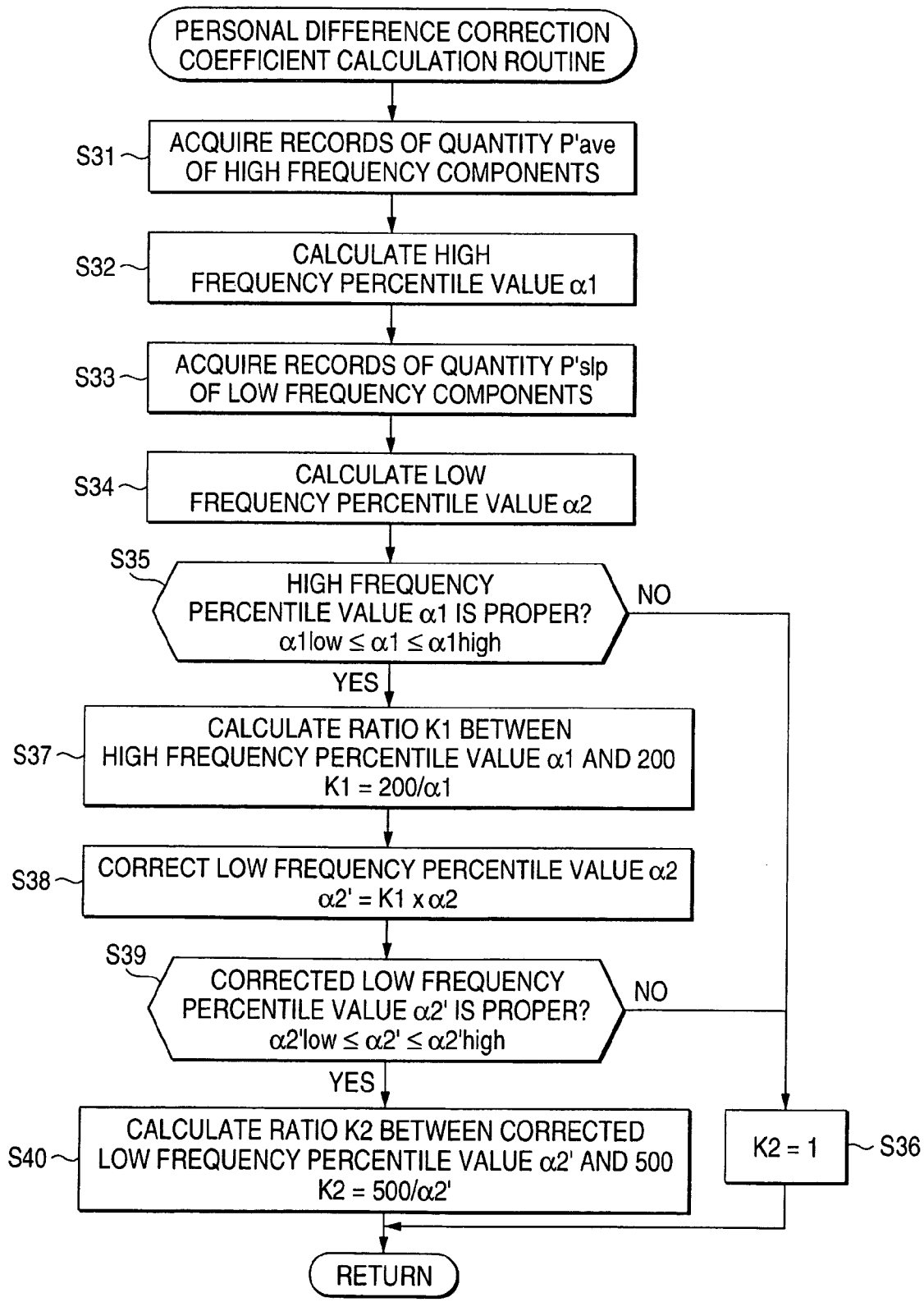
FIG. 7 is a flow chart showing a personal difference correction coefficient calculation routine.

The correction coefficient K2 is calculated according to a correction coefficient calculation routine that is shown in FIG. 7. First, at step S31, records of the quantity P'ave of high frequency components stored in a shift register are acquired. In the present embodiment, the number of the records of the quantity P'ave of high frequency components acquired is 500 samples.

When the process proceeds to step S32, a high frequency percentile value α1 is calculated based on the quantity P'ave of high frequency components.

Figure 10:
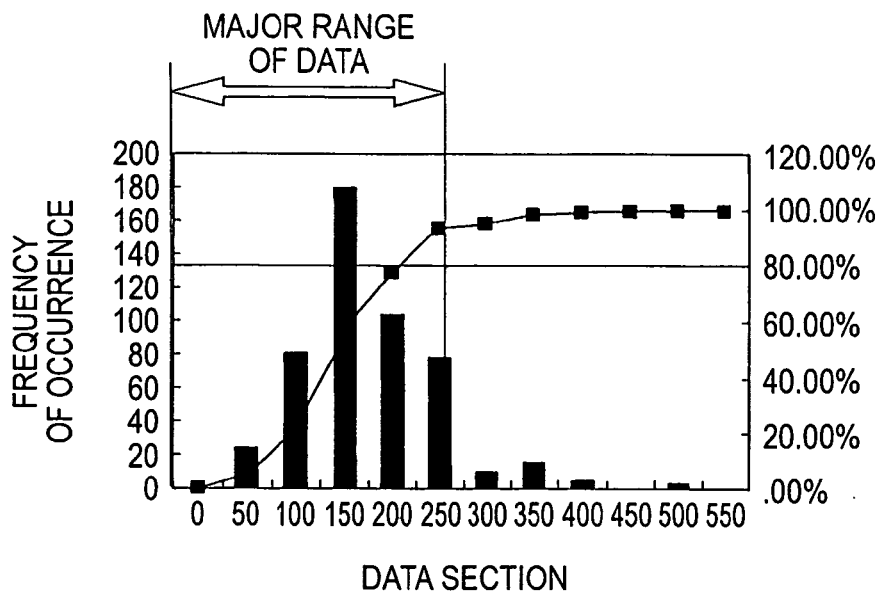
FIG. 10 is a graph for explaining a high frequency percentile value.

A method of calculating the high frequency percentile value α1 will be described with reference to FIG. 10. First, a histogram of the quantity P'ave of high frequency components is created for the samples acquired. When the sum of frequencies of occurrence of the quantities of frequency power components in the histogram counted from the smallest quantity reaches a predetermined ratio to the sum total of such frequencies, the value of the sum is chosen as the high frequency percentile value α1.

In the present embodiment, the ratio is set at 80% to calculate an 80-percentile value of the quantity P'ave of high frequency components. In other words, the high frequency percentile value α1 thus calculated is a threshold equivalent to 80% of the quantities of frequency power components counted from the smallest quantity. Abnormal values are eliminated from the histogram by the use of the threshold to allow a major range of data in the histogram to approach a normal distribution.

Next, at step S33, records of the quantity P'slp of low frequency components stored in a shift register are acquired. In the present embodiment, the number of the records of the quantity P'slp of low frequency components acquired is 500 samples.

Thereafter, at step S34, a low frequency percentile value α2 is calculated based on the quantity P'slp of low-frequency components.

A method of calculating the low frequency percentile value α2 will be described. First, a histogram of the quantity P'slp of low frequency components is created for the samples acquired. The quantities of frequency power components in the histogram are counted from the smallest quantity, an 80-percentile value of the quantity P'slp of low frequency components is chosen as the low frequency percentile value α2.

Next, it is determined at step S35 whether the high frequency percentile value α1 is proper or not. Specifically, it is determined whether the high frequency percentile value α1 is greater than a predetermined lower limit allow (e.g., 100) or whether the high frequency percentile value α1 is smaller than a predetermined upper limit α1high (e.g., 300). The process proceeds to step S37 if the high frequency percentile value α1 is within the range between the lower limit α1low and the upper limit α1high.

If the high frequency percentile value α1 is smaller than the lower limit allow or greater than the upper limit α1high, the high frequency percentile value α1 is determined to be improper, and the process proceeds to step S36.

Such thresholds are provided because a high frequency percentile value α1 out of the range of those values is significantly affected by factors beyond personal differences between drivers (e.g., environmental factors) and is therefore inadequate as data to make a correction on the basis of an average driver. Specifically, if a correction is made for a driver whose high frequency percentile value α1 is smaller than the lower limit αlow, there is a high possibility of an erroneous determination that the driver is at a low level of wakefulness. On the contrary, a high frequency percentile value α1 greater than the upper limit 1αhigh is likely to appear when staggerings of the vehicle are not accurately recognized or at the beginning of a travel on an expressway.

When the process proceeds to step S36, the process exits the routine after the correction coefficient K2 is set at 1. The correction coefficient K2 is read in at step S12 for calculating wakefulness H to be described later. When K2=1, no correction is made to the value P'slp/P'ave, and the value is set as wakefulness H as it is.

At step S37, a calculation is carried out to obtain a value K that is the ratio of the high frequency percentile value α1 to a standard high frequency percentile value. The standard high frequency percentile value is a value equivalent to the high frequency percentile value α1 of an average driver, and the value is set at 200 in the present embodiment.

Next, at step S38, the low frequency percentile value α2 is multiplied by the ratio K1 calculated at step S37 to calculate a corrected low frequency percentile value α2'.

Thereafter, the process proceeds to step S39 to determine whether the corrected low frequency percentile value α2' is proper or not. Specifically, it is determined whether the corrected low frequency percentile value α2' is greater than a predetermined lower limit α2' low (e.g., 400) or whether the corrected low frequency percentile value α2' is smaller than a predetermined upper limit α2'high (e.g., 500).

The process proceeds to step S30 if the corrected low frequency percentile value α2' is within the range between the lower limit α2'low and the upper limit α2'high. If the corrected low frequency percentile value α2' is smaller than the lower limit α2' low or greater than the upper limit α2' high, the corrected low frequency percentile value α2' is determined to be improper, and the process branches to step S36.

Such thresholds are provided because a corrected low frequency percentile value α2' out of the range of those values is significantly affected by factors beyond personal differences between drivers (e.g., environmental factors) and is therefore inadequate as data to make a correction on the basis of an average driver. Specifically, if a correction is made for a driver whose corrected low frequency percentile value α2' is smaller than the lower limit α2'low, there is a high possibility of an erroneous determination that the driver is at a low level of wakefulness. A corrected low frequency percentile value α2' greater than the upper limit α2' high indicates that the driver is in a continued state of reduction in wakefulness.

When the process proceeds to from step S39 to step S40, the correction coefficient K2 is calculated based on the corrected low frequency percentile value α2'. The correction coefficient K2 is calculated as the ratio of the corrected low frequency percentile value α2' to a predetermined standard low frequency percentile value, and the process exits the routine.

The standard low frequency percentile value is a value equivalent to the low frequency percentile value α2 of an average driver, and the value is set at 500 in the present embodiment.

Such a correction coefficient K2 is calculated at steps S35 to S40 to determine whether the high frequency percentile value α1 and the corrected low frequency percentile value α2' are proper or not. However, the coefficient may alternatively be calculated according to the following procedure when it is required only to calculate the value.

First, a calculation is carried out to obtain a first ratio which is the ratio of the high frequency percentile value α1 to the standard high frequency percentile value. Next, a calculation is carried out to obtain a second ratio which is the ratio of the low frequency percentile value α2' to the standard low frequency percentile value. The first and second ratios thus calculated may be integrated to obtain the correction coefficient K2.

When the process proceeds to step S10 shown in FIG. 5, the wakefulness calculation unit M6 performs processes at steps S10 to S12.

First, a lower limit of the quantity P'ave of high frequency components is determined at step S10. When the quantity P'ave of high frequency components is smaller than a preset lower limit value Plow (e.g., 100) (P'ave<Plow), it is determined that the driver is in a stable state of wakefulness, and the process proceeds to step S11 to set the quantity P'ave of high frequency components at the lower limit value Plow (P'ave←Plow).

As a result, when wakefulness H is calculated at step S12, wakefulness H is prevented from becoming inadequately high because of a too small denominator (an increase in wakefulness H means a reduction in the level of wakefulness)

If the quantity P'ave of high frequency components is equal to or greater than the lower limit Plow (P'ave≦Plow), the process jumps to step S12.

When the process proceeds to step S12, the process exits the routine after wakefulness H is calculated based on the following equation. The wakefulness H is instantaneous wakefulness which reflects no time-dependent factor, and it is calculated by correcting the ratio between the quantity P'ave of high frequency components and the quantity P'slp of low frequency components using the correction coefficient K2 and the road-shape-based wakefulness correction coefficient R_hosei. When the high frequency percentile value α1 and the corrected low frequency percentile value α'2 are determined to be abnormal as described above, the correction coefficient K2 is set at 1 at step S36. Wakefulness H thus calculated is equivalent to wakefulness H calculated without the correction with the correction coefficient K2.

$$H=(P'slp \times R\_hosei \times K2)/P'ave \times 100 \qquad \text{Equation 3}$$

Figure 6:
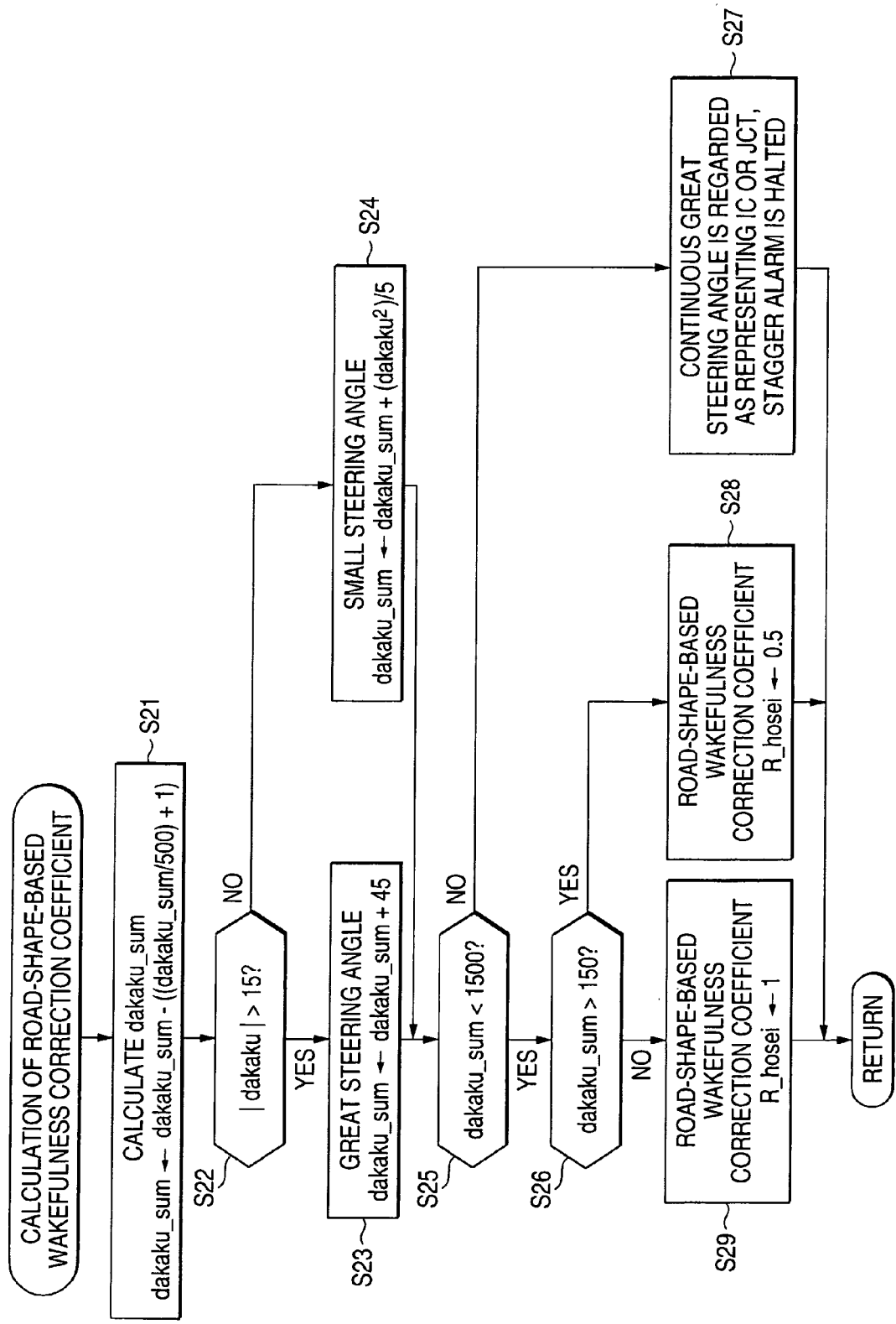
FIG. 6 is a flow chart showing a road-shape-based wakefulness correction coefficient calculation routine.

When the stagger alarm is halted at step S27 in FIG. 6, the wakefulness H is not calculated.

The value of the wakefulness H is small when the driver is wakeful as shown in FIG. 9B because the quantity P'slp of low frequency components (P'[4] or P'[5]) is small. On the contrary, when the wakefulness of the driver is low, the value of the wakefulness H is great because there is an increase in the quantity P'slp of low frequency components. Thus, the wakefulness H has a value in which the wakefulness of the driver is reflected.

The road-shape-based wakefulness correction coefficient R_hosei is a value which is set according to the shape of the expressway. When there are consecutive curves in different directions, since the road-shape-based wakefulness correction coefficient R_hosei is set at 0.5 (see step S28 in FIG. 6), the wakefulness H is 50% lower than the normal value. As a result, the 80-percentile value during the travel on the curves whose direction successively changes is corrected to a value equivalent to that for a straight travel as indicated by the arrow in FIG. 3D to prevent any erroneous determination attributable to staggering.

Figure 8:
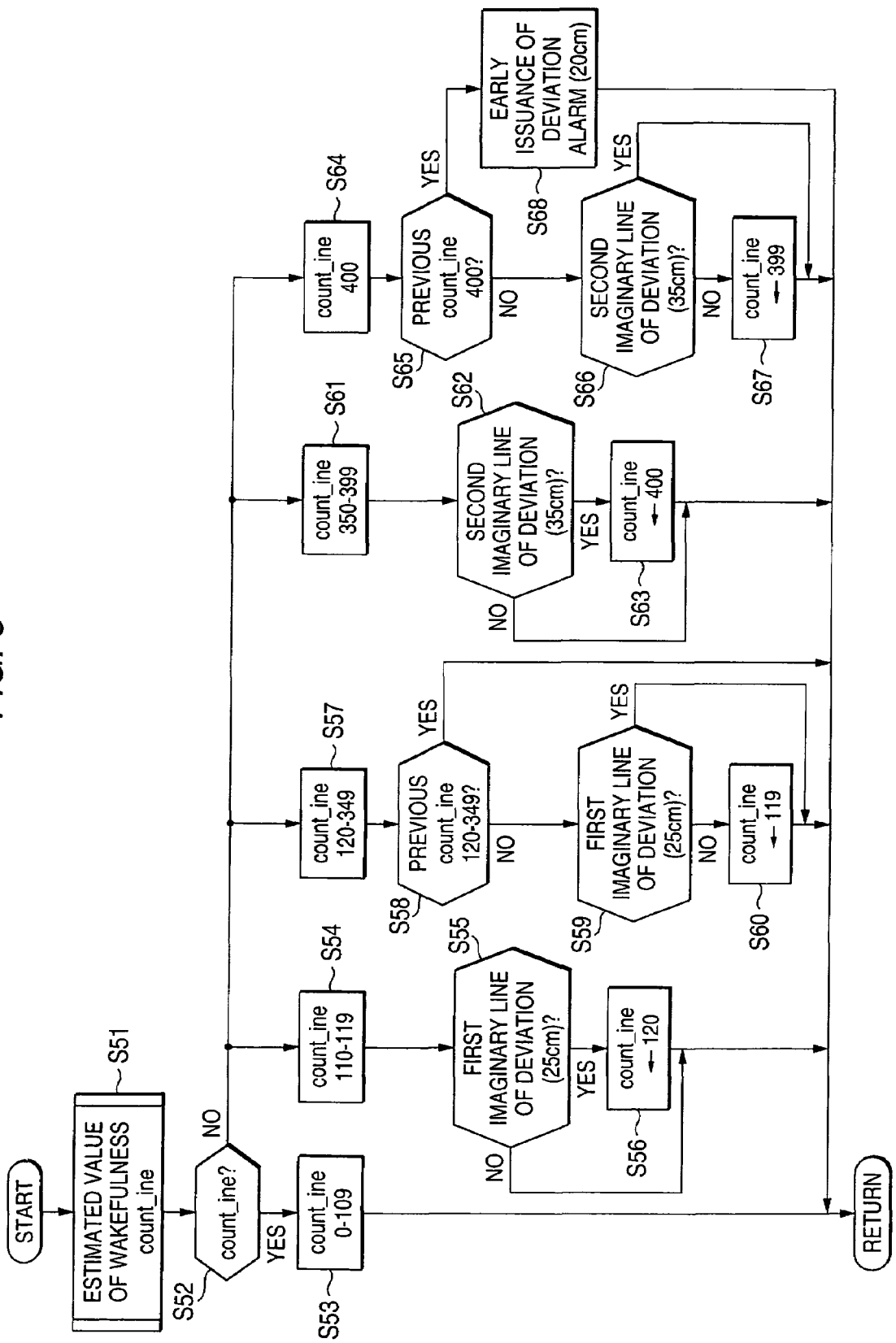
FIG. 8 is a flow chart showing an alarm determination routine.

Next, processes at the alarm control unit M7 are performed. The alarm determination routine shown in FIG. 8 is executed. First, an estimated value of wakefulness count_ine is calculated at step S51.

Referring to the calculation of the estimated value of wakefulness count_ine, step values $\beta 1$ to $\beta 9$ are set from Table 1 below based on the wakefulness H calculated at step S12 in FIG. 5. The step values $\beta 1$ to $\beta 9$ are in a non-linear relationship that satisfies $|\beta 1|>|\beta 2|>|\beta 3|>=\beta 4|>|\beta 5|$ and $|\beta 6|<|\beta 7|<|\beta 8|<|\beta 9|$ in order to vary the estimated value of wakefulness count_ine in a quantity in accordance with the value of the wakefulness H.

(Setting of Step Values $\beta$)

TABLE 1

| Wakefulness H | Step Values $\beta$ |
| --- | --- |
| ≧600 | $\beta 1$ |
| ≧500 | $\beta 2$ |
| ≧400 | $\beta 3$ |
| ≧300 | $\beta 4$ |
| ≧200 | $\beta 5$ |
| ≧150 | $\beta 6$ |
| ≧100 | $\beta 7$ |
| ≧50 | $\beta 8$ |
| ≧0 | $\beta 9$ |

Referring to the setting of the step values $\beta 1$ to $\beta 9$ in the present embodiment, $\beta 1=+50$; $\beta 2=+32$; $\beta 3=+16$; $\beta 4=+8$; $\beta 5=+4$; $\beta 6=-2$; $\beta 7=-4$; $\beta 8=-8$; and $\beta 9=-16$.

The estimated value of wakefulness count_ine is updated by adding or subtracting the current step value $\beta$ to or from the estimated value of wakefulness count_ine (count_ine←count_ine±$\beta$) It should be noted that an upper limit 400 is set for the value count_ine.

Thereafter, the process proceeds to step S52 at which the level of wakefulness of the driver is determined based on the estimated wakefulness count_ine, and a stagger alarm is issued according to the level. In the present embodiment, the following five modes are set for respective levels of wakefulness.

0≦count_ine≦109: normal state

110≦count_ine—119: first alarm standby state

120≦count_ine≦349: first alarm state

350≦count_ine≦399: second alarm standby state count_ine=400: second alarm state

When 0≦count_ine≦109, the driving is in a normal state, and the process exits the routine at step S53 without any further action based on a determination that the driver is at a normal level of wakefulness.

When 110≦count_ine≦119, it is determined that the driver is in a sleepy state at a reduced level of wakefulness, and the process proceeds to step S54 to enter a first alarm standby state.

Figure 11:
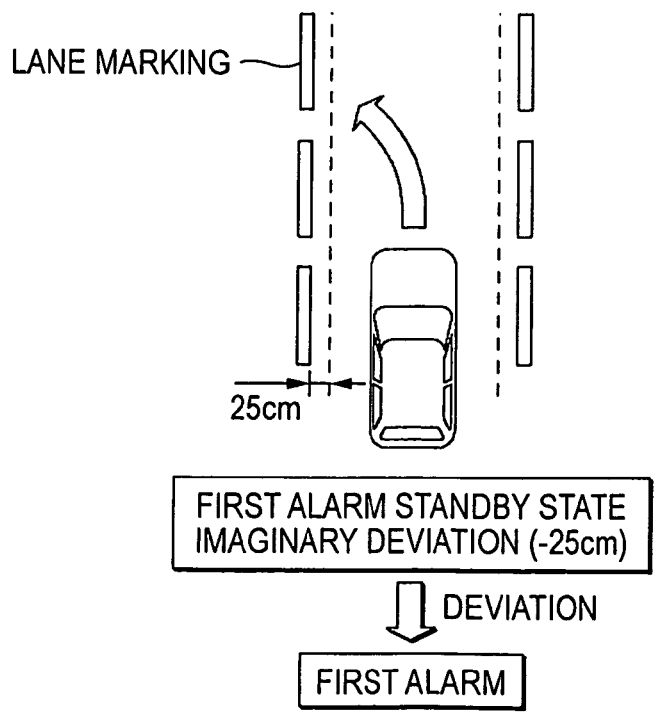
FIG. 11 is an illustration of a first alarm standby state.

The process then proceeds to step S55 at which a first-order deviation is determined. In the present embodiment, an imaginary line of first-order deviation as a first imaginary deviation line is set in a position that is 25 cm inside a lane marking as shown in FIG. 11, and it is checked whether the vehicle has exceeded the imaginary line of first-order deviation or not.

When the estimated value of wakefulness is in the range expressed by 110≦count_ine≦119, the driver is sleepy, and the vehicle stagers slightly. In this case, the driver can be alerted and made to avoid stagger easily when the imaginary line of first-order deviation is exceeded even if the imaginary line of first-order deviation is set in a position that is relatively close to the lane marking. Therefore, when there is a slight reduction of the level of wakefulness as thus described, it is possible to avoid giving the driver an uncomfortable feel by keeping an alarm on standby until the vehicle deviates from the imaginary line of first-order deviation instead of alerting the driver indiscreetly.

When the vehicle has not exceeded the imaginary line of first-order deviation, the process exits the routine, and the first alarm standby state is maintained. When the vehicle has exceeded the imaginary line of first-order deviation, the process proceeds to step S56 at which it exits the routine after the estimated value of wakefulness count_ine is set at 120 (count_ine←120).

When the vehicle exceeds the imaginary line of first-order deviation, a first alarm is activated. The first alarm only notifies the driver of the fact that the vehicle is staggering. For example, characters that read "Beware of stagger" are shown on a monitor provided on a car navigation system, and a voice message saying "The car is staggering" is output from an audio speaker at the same time.

When it is determined at step S52 that 120≦count_ine≦349, the process proceeds to step S57 to enter a first alarm state. For example, when the vehicle deviates from the imaginary line of first-order deviation, since the estimated value of wakefulness count_ine is set at 120 at step S56, the process proceeds to step S56 to enter the first alarm state in which the level of wakefulness of the driver is monitored.

First, the previous estimated value of wakefulness count_ine is checked at step S58. When the previous value has also satisfied 120≦count_ine≦349, the first alarm standby state has already been entered at the time of execution of the routine before last. Otherwise, the apparatus is currently in the first alarm state. Therefore, the process exits the routine without any further action to maintain the current state.

When the previous estimated value of wakefulness count_ine is out of the range 120≦count_ine≦349 or when the routine is being executed for the first time after the first alarm state has been entered, the process proceeds to step S59 to monitor whether the vehicle has exceeded the imaginary line of first-order deviation.

When deviation from the imaginary line of first-order deviation has occurred at the previous execution of the routine and still continues with the estimated value of wakefulness count_ine set at 120 at step S56, the process exits the routine without any action to keep the first alarm in the operating state. Alternatively, the first alarm is activated when deviation is detected for the first time at this point.

When the vehicle is returned to its normal traveling lane or when the vehicle has not exceeded the imaginary line of first-order deviation at step S59, the process proceeds to step S60 at which it exits the routine after returning the estimated value of wakefulness count_ine to 119 (count_ine←119) As a result, the process proceeds to step S54 to enter the first alarm standby state at the next execution of the routine.

When the process proceeds to step S61 based on a determination at step S52 that the estimated value of wakefulness count_ine is in the range expressed by 350≦count_ine≦399, a second alarm standby state is entered. The process then proceeds to step S62 to monitor whether the vehicle has deviated from an imaginary line of second-order deviation as a second imaginary deviation line.

When no deviation from the imaginary line of second-order deviation has occurred, the process exits the routine without any action to maintain the second alarm standby state. Therefore, the second alarm will not be issued until the vehicle deviates from the imaginary line of second-order deviation even if a reduction of the level of wakefulness of the driver is detected.

When a deviation from the imaginary line of second-order deviation has occurred, the process proceeds to step S63 at which it exits the routine after setting the estimated value of wakefulness count_ine at 400 (count_ine←400)

Figure 12:
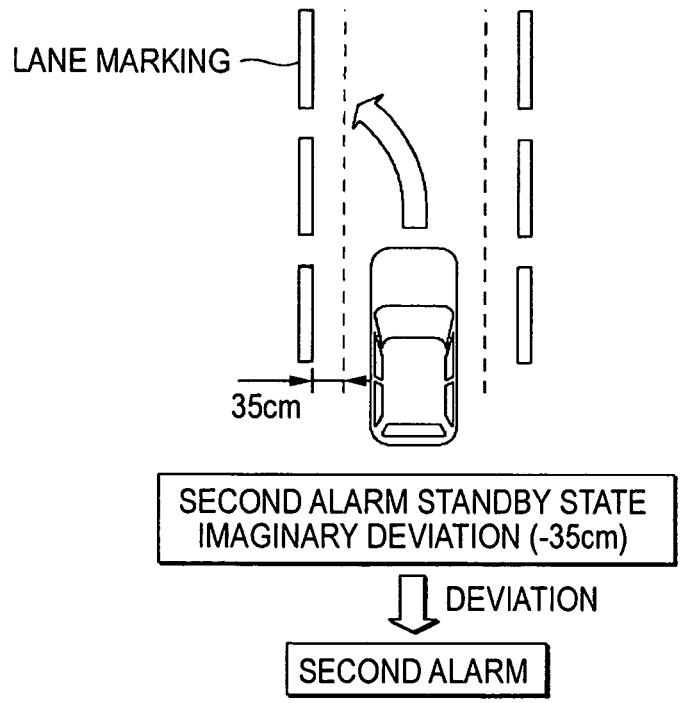
FIG. 12 is an illustration of a second alarm standby state.

An estimated value of wakefulness count_ine in the range from 350 to 399 indicates that the driver is very much sleepy, and it is assumed that relatively great staggers are occurring. In such a state, the driver is at a low level of consciousness, and a delay is likely to occur in response time. Therefore, the imaginary line of second-order deviation is set in a position at a relatively great distance (35 cm) from the lane marking as shown in FIG. 12, and alarming is performed at earlier timing.

The second alarm is activated when the vehicle has deviated from the imaginary line of second-order deviation. Since the second alarm must be an alarm that strongly alerts the driver, for example, characters reading "Beware of stagger" are displayed in red and blinked on a monitor provided on a car navigation system. At the same time, a sound message saying "pi-pi-pi vehicle is staggering!" is output from an audio speaker.

When it is determined at step S52 that the estimated value of wakefulness count_ine is 400, the process proceeds to step S64 to enter a second alarm state. The process then proceeds to step S65 to check the previous estimated value of wakefulness count_ine. For example, when the routine is executed for the first time after the estimated value of wakefulness count_ine is set at 400 at step S63, the process proceeds to step S66. At this time, if the vehicle has exceeded the imaginary line of second-order deviation, the process exits the routine with the current state maintained.

When the vehicle has been returned to the normal traveling lane or has not exceeded the imaginary line of second-order deviation, the process proceeds to step S67 at which it exits the routine after returning the estimated value of wakefulness count_ine to 399 (count_ine←399). Similarly, when the process has branched to step S65 because the estimated value of wakefulness count_ine calculated at step S51 was at the upper limit of 400 from the beginning, the process proceeds from step S65 to step S66. If no deviation from the imaginary line of second-order deviation has occurred at that time, the estimated value of wakefulness count_ine is returned to 399 at step S67. As a result, the process proceeds to step S61 to enter the second alarm standby state at the next execution of the routine.

When it is determined at step S65 that the previous estimated value of wakefulness count_ine has been 400 or when the driver continuously stays in a state at a low level of wakefulness in which he or she feels very sleepy, the process proceeds to step S68 at which it exits the routine after setting a mode in which a deviation alarm is sounded at earlier timing.

In the present embodiment, the maximum value of the estimated wakefulness count_ine is set at 400; the apparatus stands by at a level in the excess of that value until a preset line for early issuance of a deviation alarm, as a third imaginary deviation line, is exceeded regardless of the level of wakefulness of the driver; and a lane deviation alarm is activated when a deviation from the line for early issuance of the deviation alarm occurs.

The lane deviation alarm is provided by blinking characters that read "Look a head" on a monitor and by sounding an alarm tone.

Figure 13:
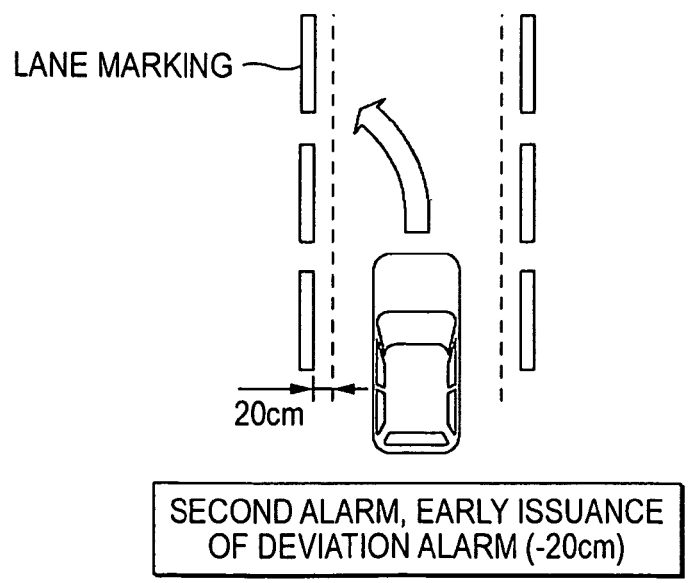
FIG. 13 is an illustration of a second alarm and a state in which a deviation alarm is issued at early timing.

As shown in FIG. 13, in the present embodiment, the line for early issuance of the deviation alarm is set in a position which is 20 cm inside the lane marking.

"Research and Study on Time of Human Response to an Alarm", Article No. J99-8, March, 2000 issued by Japan Automobile Research Institute discloses that a great deviation from a lane marking can be prevented by sounding a lane deviation alarm when the vehicle is 20 cm (0.2 m/s×1 s) inside the lane marking. It can therefore be anticipated that an ultimate quantity of a deviation of a vehicle can be suppressed to the same level as that in a wakeful state of the driver by activating a deviation alarm when the driver is driving with great stagger at a low level of wakefulness.

As thus described, in the present embodiment, the problem of the magnitudes of the quantity P'ave of high frequency components and the quantity P'slp of low frequency components attributable to personal differences between drivers can be eliminated by correcting wakefulness H using the correction coefficient K2. Since this allows various drivers as shown in FIGS. 1A to 2B to be treated similarly to an average driver, the problem of erroneous determinations attributable to personal differences between drivers can be eliminated, and the level of wakefulness of a driver can be more accurately determined.

In the present embodiment, when the high frequency percentile value α1 and the corrected low frequency percentile value α2' are determined to be improper, the wakefulness H is calculated without making a correction using the correction coefficient K2 (which is the same as setting the coefficient K2 at 1). Since the wakefulness H is calculated in such a manner, it is possible to avoid problems that occur when the calculation of the wakefulness H is attempted by correcting even significant influences of environmental factors.

The wakefulness H is calculated with a lower limit set for the level of the quantity P'ave of high frequency components as described above. Since this prevents the denominator in Equation 3 for calculating the wakefulness H from becoming excessively smaller than the quantity P'ave, the wakefulness can be accurately estimated without any influence of slight disturbances during a high speed travel and the pattern of driving unique to each driver.

In the present embodiment, when the peak of power in a frequency range including the stagger frequency f1 becomes more obvious than power in other frequency ranges because of lateral displacements or stagger of the vehicle, a reduction of the wakefulness of the driver is detected. Such detection means makes it possible to prevent any erroneous determination of wakefulness even in a situation in which the quantities of lateral displacements are generally small during a stable travel at a high speed or a situation in which the vehicle receives light lateral wind or passes by a large vehicle.

Further, steering angles are integrated, and a correction is made to decrease the quantity P' slp of low frequency components that is associated with wakefulness based on a determination that the vehicle is traveling on an expressway having consecutive curves when steering is successively performed at small steering angles. It is therefore possible to avoid erroneous determinations attributable to road shapes during a travel on successive curves at a high speed.

Even when a reduction of the level of wakefulness is detected, only monitoring is performed and no alarm is issued until a deviation from an imaginary deviation line set inside a lane marking occurs. As a result, an alarm in accordance with the level of wakefulness can be issued at constant timing, which makes it possible to avoid giving a driver an uncomfortable feel.

Since the timing of alarming can be varied depending on the level of wakefulness, the amount of a deviation of the vehicle can be minimized.

What is claimed is:

1. An apparatus for estimating wakefulness of a driver comprising:
    a frequency analyzing process unit, for calculating an average value of a quantities of the frequency power components as a quantity of high frequency components, wherein the quantities of the frequency power components are calculated by a frequency transformation of displacements of a vehicle in the width direction detected as a time series, and for calculating a maximum value of the quantities of frequency power components within a predetermined frequency range as a quantity of low frequency components, wherein the predetermined frequency range includes a stagger frequency exposed when the driver is at a low level of wakefulness;
    an estimated wakefulness value calculation unit for calculating an estimated value of wakefulness from the ratio of the quantity of high frequency components to the quantity of low frequency components; and
    an alarm control unit for setting an imaginary deviation line between a lane marking extending on a side the vehicle and the vehicle with a predetermined interval from the lane marking according to the estimated value of wakefulness and issues an alarm when a deviation from the imaginary deviation line occurs.

2. The apparatus for estimating wakefulness of a driver according to claim 1, wherein the alarm control unit sets a plurality of the imaginary deviation lines based on the estimated value of wakefulness.

3. The apparatus for estimating wakefulness of a driver according to claim 2, wherein the alarm control unit sets first and second imaginary deviation lines according to the estimated value of wakefulness,
    the first imaginary deviation line is set in a position inside and near the lane marking when the driver is at a level of wakefulness lower than that in a normal state of driving, and
    the second imaginary deviation line is set more inward from the lane marking than the first imaginary deviation line.

4. The apparatus for estimating wakefulness of a driver according to claim 2, wherein the alarm control unit sets a first alarm for warning the driver of a stagger and a second alarm for warning the driver of a deviation from the lane marking according to the estimated value of wakefulness,
    the first imaginary deviation line is set in a position inside and near the lane marking when the driver is at a level of wakefulness lower than that in a normal state of driving,
    the second imaginary deviation line is set n more inward from the lane marking than the first imaginary deviation line, and
    wherein the alarm control unit activates the first alarm when the vehicle deviates from the first imaginary deviation line, and activates the second alarm when the vehicle deviates from the second imaginary deviation line.

5. The apparatus for estimating wakefulness of a driver according to claim 4, wherein the alarm control unit sets a third imaginary deviation line different from the first and second imaginary deviation lines when the wakefulness is lower than a predetermined level after a deviation from the second imaginary deviation line has occurred, and activates a lane marking deviation alarm when the vehicle deviates from the third imaginary deviation line.

6. The apparatus for estimating wakefulness of a driver according to claim 5, wherein the third imaginary deviation line is set inside the lane marking at a distance of 20 cm therefrom.

7. A method of estimating wakefulness of a driver based on a calculated level of wakefulness comprising:
    a first step for calculating quantities of frequency power components by a frequency transformation of displacements of a vehicle in the width direction detected as a time series;
    a second step for calculating an average value of the quantities of frequency power components calculated in the first step as a quantity of high frequency components;
    a third step for calculating a maximum value of the quantities of frequency power components within a predetermined frequency range as a quantity of low frequency components, wherein the predetermined frequency range includes a stagger frequency exposed when the driver is at a low level of wakefulness;
    a fourth step for calculating an estimated value of wakefulness from the ratio of the quantity of high frequency components to the quantity of low frequency components; and
    a fifth step for setting an imaginary deviation line between a lane marking extending on a side of the vehicle and the vehicle according to the estimated value of wakefulness and issuing an alarm when a deviation from the imaginary deviation line occurs.

8. The method of estimating wakefulness of a driver according to claim 7, wherein a plurality of the imaginary deviation lines is set based on the estimated value of wakefulness at the fifth step.

9. The method of estimating wakefulness of a driver according to claim 8, wherein, at the fifth step, first and second imaginary deviation lines are set according to the estimated value of wakefulness;
    the first imaginary deviation line is set in a position inside and near the lane marking when the driver is at a level of wakefulness lower than that in a normal state of driving; and
    the second imaginary deviation line is set more inward from the lane marking than the first imaginary deviation line when a still lower level of wakefulness is determined.

10. The method of estimating wakefulness of a driver according to claim 8, wherein, at the fifth step, a first alarm for warning the driver of a stagger and a second alarm for warning the driver of a deviation from the lane marking are set according to the estimated value of wakefulness, the first imaginary deviation line is set in a position inside and near the lane marking when the driver is at a level of wakefulness lower than that in a normal state of driving, the second imaginary deviation line is set more inwardly from the lane marking than the first imaginary deviation line, and wherein the first alarm is activated when the vehicle deviates from the first imaginary deviation line, and the second alarm is activated when the vehicle deviates from the second imaginary deviation line.

11. The method of estimating wakefulness of a driver according to claim 10, wherein the alarm control unit sets a third imaginary deviation line different from the first and second imaginary deviation lines when the wakefulness is lower than a predetermined level after a deviation from the second imaginary deviation line has occurred, and activates a lane marking deviation alarm when the vehicle deviates from the third imaginary deviation line.

12. The method of estimating wakefulness of a driver according to claim 11, wherein the third imaginary deviation line is set inside the lane marking at a distance of 20 cm therefrom.

* * * * *